(12) United States Patent
Kitado et al.

(10) Patent No.: US 6,589,770 B1
(45) Date of Patent: Jul. 8, 2003

(54) KERATINOCYTE DERIVED PROTEASE

(75) Inventors: Haruo Kitado, Takatsuki (JP); Akikazu Yoshikawa, Kobe (JP); Tomoko Zaiki, Kobe (JP)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/509,908

(22) PCT Filed: Oct. 3, 1997

(86) PCT No.: PCT/US97/17864

§ 371 (c)(1),
(2), (4) Date: Apr. 3, 2000

(87) PCT Pub. No.: WO99/18219

PCT Pub. Date: Apr. 15, 1999

(51) Int. Cl.[7] ........................... C12N 9/64; C12N 15/57; C12N 15/85; A61K 38/48
(52) U.S. Cl. .................. 435/226; 435/69.1; 435/252.3; 435/320.1; 536/23.2; 424/94.64
(58) Field of Search ............................... 435/69.1, 226, 435/252.3, 320.1; 424/94.64; 536/23.2

(56) References Cited

U.S. PATENT DOCUMENTS 5,786,148 A * 7/1998 Bandman et al. .............. 435/6
5,834,290 A * 11/1998 Egelrud et al. .............. 435/226
5,962,300 A * 10/1999 Hillman et al. .............. 435/219

FOREIGN PATENT DOCUMENTS

WO  95/00651  1/1995  ........... C12N/15/57

OTHER PUBLICATIONS

Hillier, L., et al., "Generation and Analysis of 280,000 Human Expressed Sequence Tags," Genome Research, vol. 6, No. 9, Sep. 1996, pp. 807–828.
Genbank Database, Accession No. W73168, Hillier, L. et al., "The WashU–Merck EST Project", Jun. 1996.

* cited by examiner

Primary Examiner—Ponnathapu Achutamurthy
Assistant Examiner—William W. Moore
(74) Attorney, Agent, or Firm—Brahm J. Corstanje; Andrew A. Paul

(57) ABSTRACT

Disclosed is an isolated polypeptide comprising an amino acid sequence substantially as shown in SEQ ID NO:2, or substantially similar to an amino acid sequence encoded by a nucleotide sequence in a plasmid having all the identifying characteristics of Deposit No. FERM BP-6129. Also disclosed is an isolated polynucleotide substantially as shown in SEQ ID NO:1, or substantially similar to a nucleotide sequence contained in a plasmid having all of the identifying characteristics of Deposit No. FERM BP-6129. Further disclosed is an expression system comprising the above polynucleotide. Further disclosed is a composition comprising the above polypeptide.

7 Claims, No Drawings

SEQUENCE LISTING (1) GENERAL INFORMATION:

(iii) NUMBER OF SEQUENCES: 2

(2) INFORMATION FOR SEQ ID NO: 1:

(i) SEQUENCE CHARACTERISTICS:
      (A) LENGTH: 1499 base pairs
      (B) TYPE: nucleic acid
      (C) STRANDEDNESS: single
      (D) TOPOLOGY: linear (ii) MOLECULE TYPE: DNA (genomic)

(ix) FEATURE:
    (A) NAME/KEY: CDS
    (B) LOCATION: 291..1172

(ix) FEATURE:
    (A) NAME/KEY: mat_peptide
    (B) LOCATION: 489..1172

(ix) FEATURE:
    (A) NAME/KEY: 5'UTR
    (B) LOCATION: 1..290

(ix) FEATURE:
    (A) NAME/KEY: 3'UTR
    (B) LOCATION: 1173..1499

(xi) SEQUENCE DESCRIPTION: SEQ ID NO: 1:

```
CGGCCAGGAA GGCACAGGCC TGAGAAGTCT GCGGCTGAGC TGGGAGCAAA TCCCCCACCC      60

CCTACCTGGG GGACAGGGCA AGTGAGACCT GGTGAGGGTG GCTCAGCAGG AAGGAAGGAG     120

AGGTGTCTGT GCGTCCTGCA CCCACATCTT TCTCTGTCCC CTCCTTGCCC TGTCTGGAGG     180

CTGCTAGACT CCTATCTTCT GAATTCTATA GTGCCTGGGT CTCAGCGCAG TGCCGATGGT     240

GGCCCGTCCT TGTGGTTCCT CTCTACTTGG GGAAATCAGG TGCAGCGGCC ATG GCT       296
                                                       Met Ala
                                                       -66 -65

ACA GCA AGA CCC CCC TGG ATG TGG GTG CTC TGT GCT CTG ATC ACA GCC      344
Thr Ala Arg Pro Pro Trp Met Trp Val Leu Cys Ala Leu Ile Thr Ala
            -60             -55                 -50

TTG CTT CTG GGG GTC ACA GAG CAT GTT CTC GCC AAC AAT GAT GTT TCC      392
Leu Leu Leu Gly Val Thr Glu His Val Leu Ala Asn Asn Asp Val Ser
        -45             -40                 -35

TGT GAC CAC CCC TCT AAC ACC GTG CCC TCT GGG AGC AAC CAG GAC CTG      440
Cys Asp His Pro Ser Asn Thr Val Pro Ser Gly Ser Asn Gln Asp Leu
        -30             -25                 -20

GGA GCT GGG GCC GGG GAA GAC GCC CGG TCG GAT GAC AGC AGC AGC CGC      488
Gly Ala Gly Ala Gly Glu Asp Ala Arg Ser Asp Asp Ser Ser Ser Arg
    -15             -10                  -5

ATC ATC AAT GGA TCC GAC TGC GAT ATG CAC ACC CAG CCG TGG CAG GCC      536
Ile Ile Asn Gly Ser Asp Cys Asp Met His Thr Gln Pro Trp Gln Ala
 1               5                  10                  15

GCG CTG TTG CTA AGG CCC AAC CAG CTC TAC TGC GGG GCG GTG TTG GTG      584
Ala Leu Leu Leu Arg Pro Asn Gln Leu Tyr Cys Gly Ala Val Leu Val
             20                  25                  30

CAT CCA CAG TGG CTG CTC ACG GCC GCC CAC TGC AGG AAG AAA GTT TTC      632
His Pro Gln Trp Leu Leu Thr Ala Ala His Cys Arg Lys Lys Val Phe
         35                  40                  45

AGA GTC CGT CTC GGC CAC TAC TCC CTG TCA CCA GTT TAT GAA TCT GGG      680
Arg Val Arg Leu Gly His Tyr Ser Leu Ser Pro Val Tyr Glu Ser Gly
     50                  55                  60

CAG CAG ATG TTC CAG GGG GTC AAA TCC ATC CCC CAC CCT GGC TAC TCC      728
Gln Gln Met Phe Gln Gly Val Lys Ser Ile Pro His Pro Gly Tyr Ser
 65                  70                  75                  80

CAC CCT GGC CAC TCT AAC GAC CTC ATG CTC ATC AAA CTG AAC AGA AGA      776
His Pro Gly His Ser Asn Asp Leu Met Leu Ile Lys Leu Asn Arg Arg
                 85                  90                  95

ATT CGT CCC ACT AAA GAT GTC AGA CCC ATC AAC GTC TCC TCT CAT TGT      824
Ile Arg Pro Thr Lys Asp Val Arg Pro Ile Asn Val Ser Ser His Cys
             100                 105                 110
```

```
CCC TCT GCT GGG ACA AAG TGC TTG GTG TCT GGC TGG GGG ACA ACC AAG     872
Pro Ser Ala Gly Thr Lys Cys Leu Val Ser Gly Trp Gly Thr Thr Lys
            115                 120                 125

AGC CCC CAA GTG CAC TTC CCT AAG GTC CTC CAG TGC TTG AAT ATC AGC     920
Ser Pro Gln Val His Phe Pro Lys Val Leu Gln Cys Leu Asn Ile Ser
130                 135                 140

GTG CTA AGT CAG AAA AGG TGC GAG GAT GCT TAC CCG AGA CAG ATA GAT     968
Val Leu Ser Gln Lys Arg Cys Glu Asp Ala Tyr Pro Arg Gln Ile Asp
145                 150                 155                 160

GAC ACC ATG TTC TGC GCC GGT GAC AAA GCA GGT AGA GAC TCC TGC CAG    1016
Asp Thr Met Phe Cys Ala Gly Asp Lys Ala Gly Arg Asp Ser Cys Gln
                165                 170                 175

GGT GAT TCT GGG GGG CCT GTG GTC TGC AAT GGC TCC CTG CAG GGA CTC    1064
Gly Asp Ser Gly Gly Pro Val Val Cys Asn Gly Ser Leu Gln Gly Leu
                180                 185                 190

GTG TCC TGG GGA GAT TAC CCT TGT GCC CGG CCC AAC AGA CCG GGT GTC    1112
Val Ser Trp Gly Asp Tyr Pro Cys Ala Arg Pro Asn Arg Pro Gly Val
                195                 200                 205

TAC ACG AAC CTC TGC AAG TTC ACC AAG TGG ATC CAG GAA ACC ATC CAG    1160
Tyr Thr Asn Leu Cys Lys Phe Thr Lys Trp Ile Gln Glu Thr Ile Gln
210                 215                 220

GCC AAC TCC TGA GTCATCCCAG GACTCAGCAC ACCGGCATCC CCACCTGCTG        1212
Ala Asn Ser  *
225

CAGGGACAGC CCTGACACTC CTTTCAGACC CTCATTCCTT CCCAGAGATG TTGAGAATGT  1272

TCATCTCTCC AGCCCCTGAC CCCATGTCTC CTGGACTCAG GGTCTGCTTC CCCCACATTG  1332

GGCTGACCGT GTCTCTCTAG TTGAACCCTG GAACAATTT CCAAAACTGT CCAGGGCGGG   1392

GGTTGCGTCT CAATCTCCCT GGGGCACTTT CATCCTCAAG CTCAGGGCCC ATCCCTTCTC  1452

TGCAGCTCTG ACCCAAATTT AGTCCCAGAA ATAAACTGAG AAGTGGC               1499

(2) INFORMATION FOR SEQ ID NO: 2:

(i) SEQUENCE CHARACTERISTICS:
        (A) LENGTH: 293 amino acids
        (B) TYPE: amino acid
        (D) TOPOLOGY: linear (ii) MOLECULE TYPE: protein (xi) SEQUENCE DESCRIPTION: SEQ ID NO: 2:

Met Ala Thr Ala Arg Pro Pro Trp Met Trp Val Leu Cys Ala Leu Ile
-66 -65                 -60                 -55

Thr Ala Leu Leu Leu Gly Val Thr Glu His Val Leu Ala Asn Asn Asp
-50                 -45                 -40                 -35

Val Ser Cys Asp His Pro Ser Asn Thr Val Pro Ser Gly Ser Asn Gln
                -30                 -25                 -20

Asp Leu Gly Ala Gly Ala Gly Glu Asp Ala Arg Ser Asp Ser Ser
                -15                 -10                  -5

Ser Arg Ile Ile Asn Gly Ser Asp Cys Asp Met His Thr Gln Pro Trp
              1                   5                  10

Gln Ala Ala Leu Leu Arg Pro Asn Gln Leu Tyr Cys Gly Ala Val
 15                  20                  25                 30

Leu Val His Pro Gln Trp Leu Leu Thr Ala Ala His Cys Arg Lys Lys
                 35                  40                  45

Val Phe Arg Val Arg Leu Gly His Tyr Ser Leu Ser Pro Val Tyr Glu
                 50                  55                  60
```

-continued

```
Ser Gly Gln Gln Met Phe Gln Gly Val Lys Ser Ile Pro His Pro Gly
         65                  70                  75

Tyr Ser His Pro Gly His Ser Asn Asp Leu Met Leu Ile Lys Leu Asn
     80                  85                  90

Arg Arg Ile Arg Pro Thr Lys Asp Val Arg Pro Ile Asn Val Ser Ser
 95              100                 105                     110

His Cys Pro Ser Ala Gly Thr Lys Cys Leu Val Ser Gly Trp Gly Thr
             115                 120                 125

Thr Lys Ser Pro Gln Val His Phe Pro Lys Val Leu Gln Cys Leu Asn
             130                 135                 140

Ile Ser Val Leu Ser Gln Lys Arg Cys Glu Asp Ala Tyr Pro Arg Gln
         145                 150                 155

Ile Asp Asp Thr Met Phe Cys Ala Gly Asp Lys Ala Gly Arg Asp Ser
     160                 165                 170

Cys Gln Gly Asp Ser Gly Gly Pro Val Val Cys Asn Gly Ser Leu Gln
175             180                 185                     190

Gly Leu Val Ser Trp Gly Asp Tyr Pro Cys Ala Arg Pro Asn Arg Pro
             195                 200                 205

Gly Val Tyr Thr Asn Leu Cys Lys Phe Thr Lys Trp Ile Gln Glu Thr
             210                 215                 220

Ile Gln Ala Asn Ser
             225
```

KERATINOCYTE DERIVED PROTEASE

This application is a national stage application under 35 U.S.C. §371 of international application PCT/US97/17864, filed on Oct. 3, 1997.

BACKGROUND

Proteases are enzymes which digest proteins. Proteases are employed in a variety of applications outside of their natural cellular environment.

For example, in laundry applications proteases are employed as organic catalysts that cause soils to degrade into simpler, more soluble compounds which are then readily removed by water and detergents; i.e., they operate as "stain removers".

Additionally, it has been reported that certain proteases can provide certain skin conditioning benefits. The stratum corneum is the outermost layer of the epidermis. The cells of the stratum corneum, the corneocytes, represent the end stage of the epidermal differentiation process. Corneocytes are highly resistant anucleated cells mainly consisting of keratin filaments surrounded by a cross-linked protein envelope. A fraction of epidermal cells continuously leave the proliferating basal layer and go through differentiation. Consequently, there is a continuous de novo production of corneocytes. This is balanced to give a constant and well regulated stratum corneum thickness by cell shedding at the skin surface in a process called desquamation. An imbalance between de novo production of the stratum corneum and the rate of desquamation may lead to the formation of scales on the skin surface. Such a condition is commonly seen in diseases such as psoriasis and ichtyosis. The total turnover time of human epidermis is about four to six weeks. Each epidermal cell stays approximately two weeks in the stratum corneum. Desquamation involves elimination of stratum corneum cell cohesion in superficial layers. It must occur in a way that does not interfere with the barrier function of deeper layers, which is dependent on strong intercellular cohesion. It has been reported that proteases may be involved in facilitating desquamation.

Other known uses for proteases include food processing, such as tenderizing meat, producing cheese, and seasoning; fabric processing, such as removing the "scales" from the surface of wool in order to prevent the shrinkage of fabric; and removing the gelatin from the surface of photographic film.

Unfortunately the use of a number of these known proteases is limited by their ability to cause allergic reactions in sensitive individuals, and/or their limited efficacy in various environments. Such allergic reactions can result from actual application of the protease by a sensitive user, such as in applying a skin care product. Alternatively, allergic reactions can occur in individuals intimately involved in the manufacture or packaging of products containing proteases, such as laundry detergents.

Based on the foregoing, there is a need for an alternative protease which is less immunogenic and/or provides superior proteolytic properties. There is also a need for compositions, such as skin care and/or laundry detergent compositions, comprising such a protease.

SUMMARY

The present invention is directed to an isolated polypeptide comprising an amino acid sequence substantially as shown in SEQ ID NO:2, or substantially similar to an amino acid sequence encoded by a nucleotide sequence in a plasmid having all the identifying characteristics of Deposit No. FERM BP-6129.

The present invention is further directed to an isolated polynucleotide comprising a nucleotide sequence substantially as shown in SEQ ID NO:1, or substantially similar to a nucleotide sequence contained in a plasmid having all of the identifying characteristics of Deposit No. FERM BP-6129.

The present invention is further directed to an expression system comprising the above polynucleotide.

The present invention is further directed to a composition comprising the above polypeptide.

The present invention is further directed to a method of treating or preventing skin flaking comprising topical application of a composition comprising the above polypeptide.

The present invention is further directed to an antibody specifically binding the above polypeptide.

These and other features, aspects, and advantages of the present invention will become evident to those skilled in the art from a reading of the present disclosure.

DETAILED DESCRIPTION

While the specification concludes with claims which particularly point out and distinctly claim the invention, it is believed the present invention will be better understood from the following description.

All cited references are incorporated herein by reference in their entireties. Citation of any reference is not an admission regarding any determination as to its availability as prior art to the claimed invention.

All percentages are by weight of total composition unless specifically stated otherwise.

All ratios are weight ratios unless specifically stated otherwise.

Herein, "comprising" means that other steps and other ingredients which do not affect the end result can be added. This term encompasses the terms "consisting of" and "consisting essentially of".

Herein, "isolated", in reference to the polypeptide of the present invention or polynucleotide encoding the polypeptide, means that the polypeptide or polynucleotide exists apart from the complex cellular milieu in which it naturally occurs, and the polypeptide is expressible from the polynucleotide in a cell that does not naturally express it when operably linked to the appropriate regulatory sequences. Specifically, when applied to polynucleotides (e.g., DNA), "isolated" indicates the DNA is substantially isolated with respect to (i.e., exists substantially apart from) the complex cellular milieu in which it naturally occurs, or is simply present in a different nucleic acids context from that in which it occurs in nature (for example, when cloned or in the form of a restriction fragment). Thus, the polynucleotide or polypeptide of the invention may be present in a wide variety of vectors, and/or in any of a wide variety of host cells (or other milieu, such as buffers, viruses or cellular extracts), and/or in any variety of compositions; yet still be isolated in the sense used herein in that such vector, host cell or composition is not part of the natural environment of the polynucleotide or polypeptide.

Herein, "KDP" means keratinocyte-derived protease.

Herein, "substantially as shown" or "substantially similar", with respect to a polynucleotide, means the same or sufficiently similar in structure or nucleotide sequence to encode the desired polypeptide or gene product; or with respect to a polypeptide, the same or sufficiently similar in structure or amino acid sequence to serve its principal function. In other words, a particular subject sequence (amino acid or nucleotide sequence), for example altered by mutagenesis, varies from a reference sequence by one or more substitutions, deletions or additions, the net effect of which is to retain biological activity of the reference polypeptide. Alternatively, nucleotide sequences and analogs are "substantially similar" to the specific nucleotide sequence disclosed herein if the nucleotide sequences, as a result of degeneracy in the genetic code, encode an amino acid sequence substantially similar to the reference amino acid sequence. In addition, "substantially similar" means a polypeptide that will react with antibodies generated against the polypeptide or peptides derived from the polypeptide of the invention.

The present invention relates to newly identified polynucleotides, polypeptides encoded by such polynucleotides, the use of such polynucleotides and polypeptides, the production of such polynucleotides and polypeptides, as well as compositions comprising such polypeptides.

One embodiment of the present invention is contained in DH10B(pBSIISK(+)-KDP1), an *E. coli* strain carrying a plasmid containing DNA encoding a KDP polypeptide. This material has been deposited at the Institute of Bioscience and Human-Technology Agency of Industrial Science and Technology (1–3, Higashi 1 chome Tsukuba-shi Ibaraki-ken 305, Japan) on Sep. 30, 1997. The deposited strain has been assigned Deposit No. FERM BP-6129.

The biological deposit referred to herein will be maintained under the terms of the Budapest Treaty on the International Recognition of the Deposit of Microorganisms for purposes of Patent Procedure. Consequently, the deposits are available as required by the patent laws in countries wherein counterparts of this patent application, or its progeny, are filed. However, Applicants' granting of such permission to the depository to distribute samples of the deposit does not constitute an express or implied license to practice the invention claimed in any patent issuing on the subject patent application or any other patent. The deposit(s) are provided merely as a convenience to those skilled in the art, and are not an admission that the deposited material is essential to the practice of the present invention. The nucleotide sequence of the polynucleotide contained in the deposited material, as well as the amino acid sequence of the polypeptide encoded thereby, are incorporated herein by reference in the event of any conflict with any description of sequences herein. It is noted that one of ordinary skill in the art reproducing Applicants' work from the written disclosure can discover any such sequencing conflicts using routine skill.

A. Polypeptide

One aspect of the present invention relates to an isolated polypeptide comprising an amino acid sequence substantially as shown in SEQ ID NO:2, or substantially similar to the amino acid sequence of Deposit No. FERM BP-6129 (hereinafter collectively referred to as "KDP polypeptide").

Herein "polypeptide" refers to a polymer made up of amino acids linked together to form peptide bonds, preferably forming a preproprotein, proprotein, protein or fragment thereof. Herein "preproprotein" refers to a polypeptide consisting of a signal sequence, a pro region, and a mature region; and "proprotein" refers to a polypeptide consisting of a pro region and a mature region. The polypeptide of the invention may be a recombinant polypeptide, a natural polypeptide or a synthetic polypeptide.

Herein, "the amino acid sequence of Deposit No. FERM BP-6129" means an amino acid sequence encoded by a polynucleotide having a nucleotide sequence substantially similar to a nucleotide sequence contained in a plasmid having all of the identifying characteristics of Deposit No. FERM BP-6129.

Various embodiments of the KDP polypeptide include, but are not limited to, polypeptides having an amino acid sequence as shown in: SEQ ID NO:2; as well as positions 1–227 of SEQ ID NO:2. Additional embodiments include polypeptides which comprise the "catalytic triad" of SEQ ID NO:2, i.e. positions 39–43, 86–88 and 177–185; more preferably such an embodiment comprises positions 39–185.

In another embodiment of the present invention, the KDP polypeptide is an amino acid sequence which is at least about 60% homologous to the amino acid sequence as shown in SEQ ID NO:2, as shown in the above subsequences of SEQ ID NO:2, or the amino acid sequence of Deposit No. FERM BP-6129; more preferably at least about 75%; more preferably at least about 90%; more preferably at least about 95%; more preferably at least about 99%. Preferably such homologous sequences form a polypeptide having substantially the same proteolytic activity as the polypeptide having an amino acid sequence as shown in SEQ ID NO:2, as shown in the above subsequences of SEQ ID NO:2, or the amino acid sequence of Deposit No. FERM BP-6129.

As discussed in more detail below, the KDP polypeptide may be a naturally purified product, or a product of chemical synthetic procedures, or produced by recombinant techniques from a recombinant host. Depending upon the host employed in a recombinant production procedure, the KDP polypeptide may be glycosylated or may be non-glycosylated. The KDP polypeptide may also include an initial methionine amino acid residue.

B. Polynucleotide

One aspect of the present invention relates to an isolated polynucleotide comprising a nucleotide sequence substantially as shown in SEQ ID NO:1, substantially similar to a nucleotide sequence contained in a plasmid having all of the identifying characteristics of Deposit No. FERM BP-6129, or which encodes a KDP polypeptide (hereinafter collectively referred to as "KDP polynucleotide").

Herein, "polynucleotide" refers to a polymer of DNA or RNA which can be single- or double-stranded, optionally containing synthetic, non-natural or altered nucleotide bases capable of incorporation into DNA or RNA polymers. The polynucleotide may be in the form of a separate fragment or as a component of a larger nucleotide sequence construct, which has been derived from a nucleotide sequence isolated at least once in a quantity or concentration enabling identification, manipulation, and recovery of the sequence and its component nucleotide sequences by standard biochemical methods, for example, using a cloning vector. Such sequences are preferably provided in the form of an open reading frame uninterrupted by internal nontranslated sequences (introns) which are typically present in eukaryotic genes (e.g., cDNA). Genomic DNA containing the relevant sequences could also be used. Sequences of non-translated nucleotides may be present 5' or 3+ from the open reading frame, where the same do not interfere with manipulation or expression of the coding regions. Polynucleotides encoding the polypeptide provided by this invention can be assembled from cDNA fragments and short oligonucleotide linkers, or from a series of oligonucleotides, to provide a synthetic gene which is capable of being expressed in a recombinant transcriptional unit.

The polynucleotide of the present invention embraces nucleotide sequences having any sequence so long as it encodes the KDP polypeptide. As a result of degeneracy in the genetic code, any particular amino acid sequence may be encoded by many different nucleotide sequences. The skilled artisan will appreciate that the degeneracy of the genetic code allows for differing nucleotide sequences to provide the same polypeptide. In certain cases preparing a nucleotide sequence, which encodes for the same peptide but differs from the native nucleotide sequence, provides various advantages, including: ease of sequencing or synthesis, increased expression of the peptide, and/or preference of certain heterologous hosts for certain codons over others. These practical considerations are widely known and provide embodiments that may be advantageous to the user of the invention. Thus it is clearly contemplated that the native nucleotide sequence, or nucleotide sequence listed in the Sequence Listing, or incorporated by reference are not the only embodiments or nucleotide sequences envisioned by this invention.

Various embodiments of the KDP polynucleotide include, but are not limited to, a nucleotide sequence as shown in: SEQ ID NO:1; as well as positions 291–1172 of SEQ ID NO:1, positions 536–1172 of SEQ ID NO:1, positions 1–1172 of SEQ ID NO:1, or positions 291–1499 of SEQ ID NO:1. Additional embodiments of the KDP polynucleotide comprise nucleotide sequences which encode the "catalytic triad" of SEQ ID NO:2, i.e. encode positions 39–43, 86–88 and 177–185 of the polypeptide of SEQ ID:NO:2. Stated another way, such embodiments comprise positions 603–617, 744–752 and 1017–1043 of SEQ ID NO:1; more preferably such an embodiment comprises positions 603–1043 of SEQ ID NO:1.

In another embodiment of the present invention, the KDP polynucleotide is a nucleotide sequence which is at least about 60% homologous to the nucleotide sequence as shown in SEQ ID NO:1, as shown in the above subsequences of SEQ ID NO:1, or as contained in a plasmid having all of the identifying characteristics of Deposit No. FERM BP-6129; more preferably at least about 75%; more preferably at least about 90%, more preferably at least about 95%; more preferably at least about 99%. Preferably such homologous sequences are capable of encoding a KDP polypeptide.

C. Expression System

Another aspect of the present invention relates to an expression system comprising the KDP polynucleotide. Such expression systems include recombinant expression vectors comprising the KDP polynucleotide, as well as hosts which have been genetically engineered with such recombinant expression vectors ("recombinant host").

1. Vector

Herein, "recombinant expression vector" refers to a DNA construct used to express a polynucleotide which encodes a desired polypeptide (for example, the KDP polypeptide) and which includes a transcriptional subunit comprising an assembly of 1) genetic elements having a regulatory role in gene expression, for example, promoters and enhancers, 2) a structural or coding sequence which is transcribed into mRNA and translated into protein, and 3) appropriate transcription and translation initiation and termination sequences. Using methodology well known in the art, recombinant expression vectors of the present invention can be constructed. The nature of the vector is not critical to the invention, and any vector may be used, including plasmid, virus, bacteriophage, and transposon. Possible vectors for use in the present invention include, but are not limited to, chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. Additional useful vectors include, but are not limited to: for mammalian cells, pcDNA-1 (Invitrogen, San Diego, Calif.) and pSV-SPORT 1 (Gibco-BRL, Gaithersburg, Md.); for insect cells, pBlueBac III or pBlueBacHis baculovirus vectors (Invitrogen, San Diego, Calif.); and for bacterial cells, pET-3 (Novagen, Madison, Wis.). Any other vector may be used as well, as long as it is replicable and viable in the host. The KDP polynucleotide can be present in the vector operably linked to regulatory elements.

The KDP polynucleotide may be inserted into the vector by a variety of procedures. In general, the polynucleotide is inserted into an appropriate restriction endonuclease site(s) by procedures known in the art. Such procedures and others are deemed within the scope of those skilled in the art.

The vector may preferably comprise an expression element or elements operably linked to the KDP polynucleotide to provide for expression thereof at suitable levels. Any of a wide variety of expression elements may be used. The expression element or elements may, for example, be selected from promoters, enhancers, ribosome binding sites, operators and activating sequences. Such expression elements may be regulatable, for example, inducible (via the addition of an inducer). Representative examples of useful promoters include, but are not limited to: LTR (long terminal repeat from a retrovirus) or SV40 promoter, the E. coli lac or trp promoter, the phage Lambda $P_L$ promoter, and other promoters known to control expression of genes in prokaryotic or eukaryotic cells or their viruses. The expression vector preferably also contains a ribosome binding site for translation initiation and a transcription terminator. The expression vector may also include appropriate sequences for amplifying expression.

In a preferred embodiment, the expression vector further contains one or more selectable marker genes to provide a phenotypic trait for selection of transformed host cells such as dihydrofolate reductase or neomycin resistance for eukaryotic cell cultures, or such as tetracycline or ampicillin resistance for prokaryotic cell cultures.

Useful expression vectors for bacterial use are constructed by inserting a KDP polynucleotide with suitable translation initiation and termination signals in operable reading frame with a functional promoter. The vector will preferably contain one or more phenotypic selectable markers and an origin of replication to ensure maintenance of the vector and to, if desirable, provide amplification within the host.

As a representative but nonlimiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and pGEM1 (Promega Biotec, Madison, Wis., U.S.A.). These pBR322 "backbone" sections are combined with an appropriate promoter and the KDP polypeptide to be expressed. Other suitable bacterial vectors include: pQE70, pQE60, and pQE-9 (Qiagen); pbs, pD10, phagescript, psiX174, pBluescript SK, pbsks, pNH8A, pNH16a, pNH18A, and pNH47A (Stratagene); and ptrc99a, pKK223-3, pKK233-3, pDR540, and pRIT5 (Pharmacia).

Useful expression vectors for use with yeast can comprise a yeast replication origin or fragments of DNA which are required for integration into the host's chromosomal DNA, a selectable marker, a suitable promoter and enhancer, and also any necessary ribosome binding sites, a polyadenilation site, transcriptional termination sequences and 5' flanking nontranscribed sequences. Suitable yeast expression vectors include, but are not limited to, pPIC3, pPIC3K, pPIC3.5K, pPIC9, pPIC9K, pAO815, pHIL-D2, pHIL-S1, pPICZaA, pPICZaB, and pPICZaC (Invitrogen) preferably for *Pichia pastoris;* pYES2 (Invitrogen), and the pRS series vectors (STRATAGENE) preferably for *Saccharomyces cerevisiae*.

Mammalian expression vectors will preferably comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice, and polyadenylation sites may be used to provide the necessary nontranscribed genetic elements.

Suitable mammalian vectors, by way of non-limiting example, include: pWLNEO, pOG44, pXT1, pSG (Stratagene); pSVK3, pBPV, PMSG, pSVL (Pharmacia).

2. Host

The recombinant expression vector containing the KDP polynucleotide as well as an appropriate promoter or control sequence, may be employed to transform an appropriate host to permit the recombinant host to express the KDP polypeptide.

Recombinant hosts may include bacterial, fungal, insect, plant or mammalian cells which have been transformed with a recombinant expression vector of the present invention. Recombinant hosts may also include entire plants, insects or non-human mammals which have been transformed with the recombinant expression vector. Representative examples of appropriate hosts for in vitro production include: bacterial cells such as *E. coli, Salmonella typhimurium, Bacillus subtilis,* and various species within the general Pseudombnas, Streptomyces, and Staphylococcus, although others may also be employed as a matter of choice; yeast or fungal cells such as *Pichia pastoris, Candida boidinii,* and *Saccharamyces cervisiae;* insect cells such as Drosophila and Sf9; animal cells such as the COS-7 lines of monkey kidney fibroblasts (described by Gluzman, Cell, 23:175 (1981)), C127 (mouse), 3T3 (mouse), CHO (hamster) and BHK (hamster); human cells such as HeLa. Alternatively, recombinant hosts for in vivo production in non-human mammals include, but are not limited to, cows, goats, guinea pigs, hamsters, mice, pigs, rabbits and sheep; insects including silk worm larvae; and plants. The selection of an appropriate host is deemed to be within the scope of those skilled in the art from the teachings herein.

Herein, "transformation" means introducing DNA into a cell or an organism so that the DNA is replicable, either as an extrachromosomal element or by chromosomal integrant. Depending on the host cell used, transformation is done using standard techniques appropriate to such cells. The calcium treatment employing calcium chloride, as described by Cohen, S. N., Proc. Natl. Acad. Sci. (USA), 69:2110 (1972); Mandel et al., J. Mol. Biol., 53:154 (1970); and Lilgestrom et al., Gene, 40:241–246 (1985), is generally used for prokaryotes or other cells that contain substantial cell-wall barriers. For mammalian cells without such cell walls, the calcium phosphate precipitation method of Graham and van der Eb, Virology, 52:456–457 (1978) is preferred. General aspects of mammalian cell host system transformations have been described by Axel in U.S. Pat. No. 4,399,216 issued Aug. 16, 1983. Transformations into yeast are typically carried out according to the method of Van Solingen, et al., J. Bact., 130:946 (1977) and Hsiao, et al., Proc. Natl. Acad. Sci. (USA), 76:3829 (1979). Alternatively, introduction of the expression vector into the host can be effected by calcium phosphate transfection, DEAE-Dextran mediated transfection, or electroporation as set forth in Basic Methods in Molecular Biology (D. L. Davis and I. M. Battey, (1986)). However, other methods for introducing DNA into cells such as by nuclear injection or by protoplast fusion may also be used.

D. Process for Producing KDP Polypeptide

One aspect of the invention relates to a process for producing an isolated KDP polypeptide. The process comprises inserting the KDP polynucleotide into a suitable recombinant expression vector (as described above), and then transforming a suitable host with this recombinant expression vector (as described above). The transformed host is subsequently used to express the KDP polypeptide, followed by purification of the resulting KDP polypeptide from the host.

In a preferred embodiment, the method comprises culturing a yeast host cell which has been transformed with a recombinant expression vector comprising the KDP polynucleotide. The cultured bacterial host cell is subsequently used to express the KDP polypeptide, followed by purification of the resulting KDP polypeptide from the cultured medium.

Following transformation of a suitable host strain and growth of the host strain to an appropriate cell density, the selected promoter is induced by appropriate means (e.g., temperature shift or chemical induction) and cells are cultured for an additional period. The cells are typically harvested by centrifugation, disrupted by physical or chemical means, and the resulting crude extract retained for further purification.

Microbial cells employed in expression of the KDP polypeptide can be disrupted by any convenient method, including freeze-thaw cycling, sonication, mechanical disruption, or use of cell lysing agents; such methods are well known to those skilled in the art.

The KDP polypeptide can be recovered and purified from the recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the mature protein. Finally, high performance liquid chromatography (HPLC) can be employed for final purification steps.

In an alternative embodiment, the KDP polypeptide can be synthetically produced by conventional peptide synthesizers.

E. Antibodies

Another aspect of the present invention relates to antibodies specifically binding a polypeptide comprising an amino acid sequence substantially as shown in SEQ ID NO:2, or substantially similar to the amino acid sequence of Deposit No. FERM BP-6129 (herein, "KDP antibody").

Polypeptides, their fragments or other derivatives, or analogs thereof, or cells expressing them can be used as an immunogen to produce antibodies thereto. These antibodies can be, for example, polyclonal or monoclonal antibodies. The present invention also includes chimeric, single chain, and humanized antibodies, as well as Fab fragments, or the product of a Fab expression library. Various procedures known in the art may be used for the production of such antibodies and fragments.

KDP antibodies can be obtained by direct injection of a polypeptide of the present invention into an animal or by administering the polypeptide to an animal, preferably non-human. The antibody so obtained will then bind the polypeptide itself. In this manner, even a sequence encoding only a fragment of the polypeptide can be used to generate antibodies binding the whole native polypeptide. Such KDP antibodies can then be used to isolate the KDP polypeptide from tissue expressing that KDP polypeptide.

For preparation of monoclonal antibodies, any technique which provides antibodies produced by continuous cell line cultures can be used. Examples include the hybridoma technique (Kohler and Milstein, Nature, 256:495–497 (1975)), the trioma technique, the human B-cell hybridoma technique (Kozbor et al., Immunology Today, 4:72 (1983), and the EBV-hybridoma technique to produce human monoclonal antibodies (Cole, et al., Monoclonal Antibodies and Cancer Therapy, Alan R. Liss, Inc., pp. 77–96 (1985)).

Techniques for the production of single chain antibodies (U.S. Pat. No. 4,946,778) can be adapted to produce single chain antibodies to immunogenic polypeptide products of this invention.

F. Compositions Comprising the Polypeptide

Another aspect of the present invention relates to compositions comprising the KDP polypeptide and an acceptable carrier. The composition may be any variety of composition which requires a protease component. Particularly preferred are compositions which may come in contact with humans, for example, through use or manufacture. The use of the KDP polypeptide of the present invention is believed to reduce or eliminate the immunogenic response users and/or handlers might otherwise experience with a similar composition containing a known protease, particularly a protease of non-human origin. Preferred compositions are skin care compositions and laundry detergent compositions.

Herein, "acceptable carrier" includes, but is not limited to, cosmetically-acceptable carriers, pharmaceutically-acceptable carriers, and carriers acceptable for use in cleaning compositions.

1. Skin Care Compositions

Skin care compositions of the present invention preferably comprise, in addition to the KDP polypeptide, a cosmetically- or pharmaceutically-acceptable carrier.

Herein, "cosmetically-acceptable carrier" means one or more compatible solid or liquid filler diluents or encapsulating substances which are suitable for use in contact with the skin of humans and lower animals without undue toxicity, incompatibility, instability, irritation, allergic response, and the like, commensurate with a reasonable benefit/risk ratio.

Herein, "pharmaceutically-acceptable" means one or more compatible drugs, medicaments or inert ingredients which are suitable for use in contact with the tissues of humans and lower animals without undue toxicity, incompatibility, instability, irritation, allergic response, and the like, commensurate with a reasonable benefitrisk ratio. Pharmaceutically-acceptable carriers must, of course, be of sufficiently high purity and sufficiently low toxicity to render them suitable for administration to the mammal being treated.

Herein, "compatible" means that the components of the cosmetic or pharmaceutical compositions are capable of being commingled with the KDP polypeptide, and with each other, in a manner such that there is no interaction which would substantially reduce the cosmetic or pharmaceutical efficacy of the composition under ordinary use situations.

Preferably the skin care compositions of the present invention are topical compositions., i.e., they are applied topically by the direct laying on or spreading of the composition on skin. Preferably such topical compositions comprise a cosmetically- or pharmaceutically-acceptable topical carrier.

The topical composition may be made into a wide variety of product types. These include, but are not limited to, lotions, creams, beach oils, gels, sticks, sprays, ointments, pastes, mousses, and cosmetics; hair care compositions such as shampoos and conditioners (for, e.g., treating/preventing dandruff); and personal cleansing compositions. These product types may comprise several carrier systems including, but not limited to, solutions, emulsions, gels and solids.

Preferably the carrier is a cosmetically- or pharmaceutically-acceptable aqueous or organic solvent. Water is a preferred solvent. Examples of suitable organic solvents include: propylene glycol, polyethylene glycol (200–600), polypropylene glycol (425–2025), propylene glycol-14 butyl ether, glycerol, 1,2,4-butanetriol, sorbitol esters, 1,2,6-hexanetriol, ethanol, isopropanol, butanediol, and mixtures thereof. Such solutions useful in the present invention preferably contain from about 0.001% to about 25% of the KDP polypeptide, more preferably from about 0.1% to about 10% more preferably from about 0.5% to about 5%; and preferably from about 50% to about 99.99% of an acceptable aqueous or organic solvent, more preferably from about 90% to about 99%.

Skin care compositions of the present invention may further include a wide variety of additional oil-soluble materials and/or water-soluble materials conventionally used in topical compositions, at their art-established levels. Such additional components include, but are not limited to: thickeners, pigments, fragrances, humectants, proteins and polypeptides, preservatives, opacifiers, penetration enhancing agents, collagen, hylauronic acid, elastin, hydrolysates, primrose oil, jojoba oil, epidermal growth factor, soybean saponins, mucopolysaccharides, Vitamin A and derivatives thereof, Vitamin B2, biotin, pantothenic acid, Vitamin D, and mixtures thereof.

2. Cleaning Compositions

Cleaning compositions of the present invention preferably comprise, in addition to the KDP polypeptide, a surfactant. The cleaning composition may be in a wide variety of forms, including, but not limited to, hard surface cleaning compositions, dishcare cleaning compositions, and laundry detergent compositions.

Preferred cleaning compositions are laundry detergent compositions. Such laundry detergent compositions include, but not limited to, granular, liquid and bar compositions. Preferably, the laundry detergent composition further comprises a builder.

The laundry detergent composition of the present invention contains the KDP polypeptide at a level sufficient to provide a "cleaning-effective amount". The term "cleaning effective amount" refers to any amount capable of producing a cleaning, stain removal, soil removal, whitening, deodorizing, or freshness improving effect on substrates such as fabrics, dishware and the like. In practical terms for current commercial preparations, typical amounts are up to about 5 mg by weight, more typically 0.01 mg to 3 mg, of active enzyme per gram of the detergent composition. Stated another way, the laundry detergent compositions herein will typically comprise from 0.001% to 5%, preferably 0.01%–3%, more preferably 0.01% to 1% by weight of raw KDP polypeptide preparation. Herein, "raw KDP polypeptide preparation" refers to preparations or compositions in which the KDP polypeptide is contained in prior to its addition to the laundry detergent composition. Preferably, the KDP polypeptide is present in such raw KDP polypeptide preparations at levels sufficient to provide from 0.005 to 0.1 Anson units (AU) of activity per gram of raw KDP polypeptide preparation. For certain detergents, such as in automatic dishwashing, it may be desirable to increase the active KDP polypeptide content of the raw KDP polypeptide preparation in order to minimize the total amount of non-catalytically active materials and thereby improve spotting/filming or other end-results. Higher active levels may also be desirable in highly concentrated detergent formulations.

Preferably, the laundry detergent compositions of the present invention, including but not limited to liquid compositions, may comprise from about 0.001% to about 10%, preferably from about 0.005% to about 8%, most preferably from about 0.01% to about 6%, by weight of an enzyme stabilizing system. The enzyme stabilizing system can be any stabilizing system which is compatible with the KDP polypeptide, or any other additional detersive enzymes that may be included in the composition. Such a system may be inherently provided by other formulation actives, or be added separately, e.g., by the formulator or by a manufacturer of detergent-ready enzymes. Such stabilizing systems can, for example, comprise calcium ion, boric acid, propylene glycol, short chain carboxylic acids, boronic acids, and mixtures thereof, and are designed to address different stabilization problems depending on the type and physical form of the detergent composition.

The detergent composition also comprises a detersive surfactant. Preferably the detergent composition comprises at least about 0.01% of a detersive surfactant; more preferably at least about 0.1%; more preferably at least about 1%; more preferably still, from about 1% to about 55%.

Preferred detersive surfactants are cationic, anionic, nonionic, ampholytic, zwitterionic, and mixtures thereof, further described herein below. Nonlimiting examples of detersive surfactants useful in the detergent composition include, the conventional $C_{11}$–$C_{18}$ alkyl benzene sulfonates ("LAS") and primary, branched-chain and random $C_{10}$–$C_{20}$ alkyl sulfates ("AS"), the $C_{10}$–$C_{18}$ secondary (2,3) alkyl sulfates of the formula $CH_3(CH_2)_x(CHOSO_3^-M^+)$ $CH_3$ and $CH_3(CH_2)_y(CHOSO_3^-M^+)$ $CH_2CH_3$ where x and (y+1) are integers of at least about 7, preferably at least about 9, and M is a water-solubilizing cation, especially sodium, unsaturated sulfates such as oleyl sulfate, the $C_{10}$–$C_{18}$ alkyl alkoxy sulfates ("$AE_xS$"; especially EO 1–7 ethoxy sulfates), $C_{10}$–$C_{18}$ alkyl alkoxy carboxylates (especially the EO 1–5 ethoxycarboxylates), the $C_{10}$–$C_{18}$ glycerol ethers, the $C_{10}$–$C_{18}$ alkyl polyglycosides and their corresponding sulfated polyglycosides, and $C_{12}$–$C_{18}$ alpha-sulfonated fatty acid esters. If desired, the conventional nonionic and ampho-teric surfactants such as the $C_{12}$–$C_{18}$ alkyl ethoxylates ("AE") including the so-called narrow peaked alkyl ethoxylates and $C_6$–$C_{12}$ alkyl phenol alkoxylates (especially ethoxylates and mixed ethoxy/propoxy), $C_{12}$–$C_{18}$ betaines and sulfobetaines ("sultaines"), $C_{10}$–$C_{18}$ amine oxides, and the like, can also be included in the overall compositions. The $C_{10}$–$C_{18}$ N-alkyl polyhydroxy fatty acid amides can also be used. Typical examples include the $C_{12}$–$C_{18}$ N-methylglucamides. See WO 9,206,154. Other sugar-derived surfactants include the N-alkoxy polyhydroxy fatty acid amides, such as $C_{10}$–$C_{18}$ N-(3-methoxypropyl) glucamide. The N-propyl through N-hexyl $C_{12}$–$C_{18}$ glucamides can be used for low sudsing. $C_{10}$–$C_{20}$ conventional soaps may also be used. If high sudsing is desired, the branched-chain $C_{10}$–$C_{16}$ soaps may be used. Mixtures of anionic and nonionic surfactants are especially useful. Other conventional useful surfactants are listed in standard texts.

Detergent builders are also included in the laundry detergent composition to assist in controlling mineral hardness. Inorganic as well as organic builders can be used. Builders are typically used in fabric laundering compositions to assist in the removal of particulate soils.

The level of builder can vary widely depending upon the end use of the composition and its desired physical form. When present, the compositions will typically comprise at least about 1% builder. Liquid formulations typically comprise from about 5% to about 50%, more typically about 5% to about 30%, by weight, of detergent builder. Granular formulations typically comprise from about 10% to about 80%, more typically from about 15% to about 50% by weight, of the detergent builder. Lower or higher levels of builder, however, are not meant to be excluded.

Inorganic or P-containing detergent builders include, but are not limited to, the alkali metal, ammonium and alkano-lammonium salts of polyphosphates (exemplified by the tripolyphosphates, pyrophosphates, and glassy polymeric meta-phosphates), phosphonates, phytic acid, silicates, carbonates (including bicarbonates and sesquicarbonates), sulphates, and aluminosilicates. However, non-phosphate builders are required in some locales. Importantly, the compositions herein function surprisingly well even in the presence of the so-called "weak" builders (as compared with phosphates) such as citrate, or in the so-called "underbuilt" situation that may occur with zeolite or layered silicate builders.

Examples of silicate builders are the alkali metal silicates, particularly those having a $SiO_2$:$Na_2O$ ratio in the range 1.6:1 to 3.2:1 and layered silicates, such as the layered sodium silicates described in U.S. Pat. No. 4,664,839, issued May 12, 1987 to H. P. Rieck. NaSKS-6 is the trademark for a crystalline layered silicate marketed by Hoechst (commonly abbreviated herein as "SKS-6"). Unlike zeolite builders, the Na SKS-6 silicate builder does not contain aluminum. NaSKS-6 has the delta-$Na_2SiO_5$ morphology form of layered silicate. It can be prepared by methods such as those described in German DE-A-3,417,649 and DE-A-3,742,043. SKS-6 is a highly preferred layered silicate for use herein, but other such layered silicates, such as those having the general formula $NaMSi_xO_{2x+1} \cdot yH_2O$ wherein M is sodium or hydrogen, x is a number from 1.9 to 4, preferably 2, and y is a number from 0 to 20, preferably 0 can be used herein. Various other layered silicates from Hoechst include NaSKS-5, NaSKS-7 and NaSKS-11, as the alpha, beta and gamma forms. As noted above, the delta-$Na_2SiO_5$ (NaSKS-6 form) is most preferred for use herein. Other silicates may also be useful such as for example magnesium silicate, which can serve as a crispening agent in granular formulations, as a stabilizing agent for oxygen bleaches, and as a component of suds control systems.

Examples of carbonate builders are the alkaline earth and alkali metal carbonates as disclosed in German Patent Application No. 2,321,001 published on November 15, 1973.

Aluminosilicate builders are useful in the present invention. Aluminosilicate builders are of great importance in most currently marketed heavy duty granular detergent compositions, and can also be a significant builder ingredient in liquid detergent formulations. Aluminosilicate builders include those having the empirical formula:

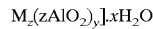

$$M_z(zAlO_2)_y] \cdot xH_2O$$

wherein z and y are integers of at least 6, the molar ratio of z to y is in the range from 1.0 to about 0.5, and x is an integer from about 15 to about 264.

Useful aluminosilicate ion exchange materials are commercially available. These aluminosilicates can be crystalline or amorphous in structure and can be naturally-occurring aluminosilicates or synthetically derived. A method for producing aluminosilicate ion exchange materials is disclosed in U.S. Pat. No. 3,985,669, Krummel, et al, issued Oct. 12, 1976. Preferred synthetic crystalline aluminosilicate ion exchange materials useful herein are available under the designations Zeolite A, Zeolite P (B), Zeolite MAP and Zeolite X. In an especially preferred embodiment, the crystalline aluminosilicate ion exchange material has the formula:

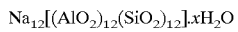

wherein x is from about 20 to about 30, especially about 27. This material is known as Zeolite A. Dehydrated zeolites (x=0–10) may also be used herein. Preferably, the aluminosilicate has a particle size of about 0.1–10 microns in diameter.

Organic detergent builders suitable for the purposes of the present invention include, but are not restricted to, a wide variety of polycarboxylate compounds. As used herein, "polycarboxylate" refers to compounds having a plurality of carboxylate groups, preferably at least 3 carboxylates. Polycarboxylate builder can generally be added to the composition in acid form, but can also be added in the form of a neutralized salt. When utilized in salt form, alkali metals, such as sodium, potassium, and lithium, or alkanolammonium salts are preferred.

Included among the polycarboxylate builders are a variety of categories of useful materials. One important category of polycarboxylate builders encompasses the ether polycarboxylates, including oxydisuccinate, as disclosed in Berg, U.S. Pat. No. 3,128,287, issued Apr. 7, 1964, and Lamberti et al., U.S. Pat. No. 3,635,830, issued Jan. 18, 1972. See also "TMS/TDS" builders of U.S. Pat. No. 4,663,071, issued to Bush et al., on May 5, 1987. Suitable ether polycarboxylates also include cyclic compounds, particularly alicyclic compounds, such as those described in U.S. Pat. No. 3,923,679 to Rapko, issued Dec. 2, 1975; U.S. Pat. No. 3,835,163 to Rapko, issued Sep. 10, 1974; U.S. Pat. No. 4,158,635 to Crutchfield et al., issued Jun. 19, 1979; U.S. Pat. No. 4,120,874 to Crutchfield et al., issued Oct. 17, 1978; and U.S. Pat. No. 4,102,903 to Crutchfield et al., issued Jul. 25, 1978.

Other useful detergency builders include the ether hydroxypolycarboxylates, copolymers of maleic anhydride with ethylene or vinyl methyl ether, 1,3,5-trihydroxy benzene-2,4,6-trisulphonic acid, and carboxymethyloxysuccinic acid, the various alkali metal, ammonium and substituted ammonium salts of polyacetic acids such as. ethylenediamine tetraacetic acid and nitrilotriacetic acid, as well as polycarboxylates such as mellitic acid, succinic acid, oxydisuccinic acid, polymaleic acid, benzene 1,3,5-tricarboxylic acid, carboxymethyloxysuccinic acid, and soluble salts thereof.

Citrate builders, e.g., citric acid and soluble salts thereof (particularly sodium salt), are polycarboxylate builders of particular importance for heavy duty liquid detergent formulations due to their availability from renewable resources and their biodegradability. Citrates can also be used in granular compositions, especially in combination with zeolite and/or layered silicate builders. Oxydisuccinates are also especially useful in such compositions and combinations.

Also suitable in the detergent compositions of the present invention are the 3,3-dicarboxy4-oxa-1,6-hexanedioates and the related compounds disclosed in U.S. Pat. No. 4,566,984 to Bush, issued Jan. 28, 1986. Useful succinic acid builders include the $C_5$–$C_{20}$ alkyl and alkenyl succinic acids and salts thereof. A particularly preferred compound of this type is dodecenylsuccinic acid. Specific examples of succinate builders include: laurylsuccinate, myristylsuccinate, palmitylsuccinate, 2-dodecenylsuccinate (preferred), 2-pentadecenylsuccinate, and the like. Laurylsuccinates are the preferred builders of this group, and are described in European Patent Application 200,263 to Barrat et al., published Nov. 5, 1986.

Other suitable polycarboxylates are disclosed in U.S. Pat. No. 4,144,226, Crutchfield et al, issued Mar. 13, 1979 and in U.S. Pat. No. 3,308,067, Diehl, issued Mar. 7, 1967. See also U.S. Pat. No. 3,723,322 to Diehl, issued Mar. 27, 1973.

Fatty acids, e.g., $C_{12}$–$C_{18}$ monocarboxylic acids, can also be incorporated into the compositions alone, or in combination with the aforesaid builders, especially citrate and/or the succinate builders, to provide additional builder activity. Such use of fatty acids will generally result in a diminution of sudsing, which should be taken into account by the formulator.

In situations where phosphorus-based builders can be used, and especially in the formulation of bars used for hand-laundering operations, the various alkali metal phosphates such as the well-known sodium tripolyphosphates, sodium pyrophosphate and sodium orthophosphate can be used. Phosphonate builders such as ethane-1-hydroxy-1,1-diphosphonate and other known phosphonates (see, for example, U.S. Pat. No. 3,159,581 to Diehl, issued Dec. 1, 1964; U.S. Pat. No. 3,213,030 to Diehl, issued Oct. 19, 1965; U.S. Pat. No. 3,400,148 to Quimby, issued Sep. 3, 1968; U.S. Pat. No. 3,422,021 to Roy, issued Jan. 14, 1969; and U.S. Pat. No. 3,422,137 to Quimby, issued Jan. 14, 1969) can also be used.

Additional components which may be used in the laundry detergent compositions of the present invention include, but are not limited to: alkoxylated polycarboxylates (to provide, e.g., additional grease stain removal performance), bleaching agents, bleach activators, bleach catalysts, brighteners, chelating agents, clay soil removal/anti-redeposition agents, dye transfer inhibiting agents, additional enzymes (including lipases, amylases, hydrolases, and other proteases), fabric softeners, polymeric soil release agents, polymeric dispersing agents, and suds suppressors, The compositions herein may further include one or more other detergent adjunct materials or other materials for assisting or enhancing cleaning performance, treatment of the substrate to be cleaned, or to modify the aesthetics of the detergent composition (e.g., perfumes, colorants, dyes, etc.). Non-limiting examples of such adjunct materials include, The detergent compositions herein may further comprise other known detergent cleaning components including alkoxylated polycarboxylates, bleaching compounds, brighteners, chelating agents, clay soil removal/anti-redeposition agents, dye transfer inhibiting agents, enzymes, enzyme stabilizing systems, fabric softeners, polymeric soil release agents, polymeric dispersing agents, suds suppressors. The detergent composition may also comprise other ingredients including carriers, hydrotropes, processing aids, dyes or pigments, solvents for liquid formulations, solid fillers for bar compositions.

G. Method of Treating or Preventing Skin Flaking

Another aspect of the present invention relates to a method of treating or preventing skin flaking. The method comprises topical application of a safe and effective amount of a composition comprising the KDP polypeptide.

Herein, "safe and effective amount" means an amount of KDP polypeptide high enough to provide a significant positive modification of the condition to be treated, but low enough to avoid serious side effects (at a reasonable benefit/ risk ratio), within the scope of sound medical judgment. A safe and effective amount of KDP polypeptide will vary with the particular condition being treated, the age and physical condition of the subject being treated, the severity of the condition, the duration of the treatment, the nature of concurrent therapy and like factors.

Suitable compositions for use in the subject method include the above-described skin care compositions, including hair care compositions (for, e.g., treating/preventing dandruff caused by skin flaking).

The following examples further describe and demonstrate the preferred embodiments within the scope of the present invention. The examples are given solely for the purpose of illustration, and are not to be construed as limitations of the present invention since many variations thereof are possible without departing from its spirit and scope.

EXAMPLE 1

This example shows the isolation of a KDP polynucleotide. A pair of oligonucleotide primers are chemically synthesized and used to amplify the coding region for the human SCCE (stratum corneum chymotrypsin-like enzyme) gene (based on the DNA sequence of the gene set forth in Hansson et al., J. Biol. Chem. 269:19420–19426, 1994) by PCR (Polymerase Chain Reaction) using a human keratinocyte cDNA library as a template. The amplified SCCE cDNA fragment is then cloned into an E. coli vector and its DNA sequence is confirmed. The cloned SCCE DNA fragment is then isolated, radio labeled with $^{32}$P, and used as a probe in a Southern hybridization experiment to screen for novel cDNA clones which have similar structures to SCCE. The hybridization experiment is carried out under the low stringency condition which provides positive signals even if the nucleotide sequence similarity is as low as approximately 70%. In one particular experiment, 11 positive clones were obtained from 1×10$^5$ lambda phage clones screened, and two of them (the clone #31 and #67) turned out to carry the same cDNA in different positions. We focused on these two. Since both the clones lacked the 5' portion of the gene, a short DNA fragment corresponding to the 5' end of the clone #67 was prepared by PCR, radio labeled with $^{32}$P, and used to screen the library again to isolate clones containing the missing portion. A total of 12 positive clones were selected from another 1×10$^5$ clones screened. DNA sequencing analysis indicated the clone named #TZ-10 contains the missing 5' portion of the cDNA and the longest 5' untranslated region among the clones. The DNA of the clone #31 and #TZ-10 were isolated and merged into a full length clone in the pBluescript II SK+ vector with appropriate restriction enzymes in combination. Comparison of the DNA sequence of the full length clone with the DNA database indicated that it encodes a novel serine protease and, therefore, we named the clone KDP1 Keratinocyte-Derived Protease 1). KDP1 is structurally similar to SCCE, trypsin nd chymotrypsin at the protein level (49%, 48% and 36%, respectively) but ignificantly different from any one of them. KDPL has the nucleotide sequence ncoding a KDP polypeptide, set forth in Deposit No. FERM BP-6129.

EXAMPLE 2

This example shows the chemical synthesis of a KDP polynucleotide. A single- or double-stranded oligonucleotide which corresponds to any desired part of the KDP1 gene of Example 1 is chemically synthesized with a nucleotide synthesizer such as ABI DNA/RNA synthesizer model 380A/380B/381A/390Z/391/392/394.

EXAMPLE 3

This example shows the formation of an expression vector containing a KDP polynucleotide. By using the recombinant PCR technique, the mature portion of the KDP1 gene is fused to an artificial pro sequence containing a repeat of six Histidine residues at the 5' end. This Histidine tag is designed for a quick purification of KDP1 protein after expression. The pro sequence also contains a specific cleavage site by Enterokinase so that the recombinant pro-KDP1 can be activated by the Enterokinase digestion after the purification step. This KDP1 gene cassette is cloned between the Xho1 and Not1 sites of the pPIC9 vector (Invitrogen) for the expression in the yeast, Pichia pastoris, cells. The cloning sites are located immediately downstream of the yeast α-factor signal sequence in the proper reading frame, so that the recombinant pro-KDP1 is designed to be secreted into the medium. The induction of pro-KDP1 protein is under the control of the AOX1 promoter which is located upstream of the yeast α-factor signal sequence. The transcription from the AOX1 promoter is strongly induced by adding methanol in the medium, and thus the recombinant KDP1 protein can be induced by methanol. The vector also contains an Ampicillin resistance gene and a HIS4 gene for the selection in E. coli and Pichia pastoris cells, respectively.

EXAMPLE 4

This example shows the transformation of a host with the expression system of Example 3. Transformation of Pichia cells is done by either the spheroplasts method or the electroporation method. (Refer to the manual of methods for expression of recombinant proteins in Pichia pastods (catalog no. K1710-01), which is distributed by Invitrogen). Pichia spheroplasts are prepared by treating GS115, KM71 or SMD1168 strains with sorbitol and Zymolyase. 10 μg of the expression plasmid DNA is added to transform the spheroplast preparation in the presence of PEG and CaCl$_2$. Spheroplasts are then plated onto Histidine-depleted plates for the selection of HIS$^+$ transformants at 28–30° C. For the electroporation method, Pichia GS115, KM71 or SMD1168 cells are grown in rich media, collected and treated with 1M sorbitol solution. After mixing cells with 5–20 μg of linearized plasmid DNA, the solution is transferred to an ice-cold 0.2 cm electroporation cuvette (Bio-Rad). The electroporation is carried out at 1,500 volts with 25 μF capacitance and 200Ω resistance with a Bio-Rad Gene Pulsar. The cells are spread onto plates to obtain HIS$^+$ transformants at 28–30° C. Linear DNA can generate stable transformants of Pichia pastoris via homologous recombination between the transforming DNA and regions of homology within the genome. Single crossover events (insertion) are much more likely than double crossover events (replacements). Since single crossover events do not destroy the AOX1 gene on the host genome, such transformants can grow well on methanol-containing plates (HIS$^+$ and Mut$^+$ phenotype). In contrast, when the gene replacement arises from a double crossover event between the AOX1 promoter and 3' AOX1 regions of the vector and genome, this results in the complete removal of the AOX1 coding region. The transformants with the resulting phenotype (HIS$^+$ Mut$^s$) can be selected by their slow growth on the methanol-containing plate. Both the Mut$^+$ and Mut$^s$ transformants are screened for KDP1 expression.

EXAMPLE 5

This example shows the expression and purification of a KDP polypeptide.

Expression: The transformants are grown in either minimal or rich media until they reach their maximum growth by either shake flask or fermentation. For the induction of the KDP1 gene, methanol is added in the medium at the maximum concentration of 1% in the case of the Mut$^s$ transformants. With the Mut⁺ transformants, methanol is added at the levels which allow the cells to maintain the dissolved oxygen levels in the medium above 20%. About 6 days after starting the methanol induction, the medium is harvested and the supernatant is collected by centrifugation.

Purification: The supernatant is applied onto a nickel-chelating column and the pro-KDP1 is adsorbed through the high affinity of the HIS tag for divalent cations. After washing unrelated proteins in the medium off the column, the pro-KDP1 protein is recovered by elution in a low pH buffer or by competition with imidazole or histidine. The eluate is concentrated by ultrafiltration and the buffer is exchanged with the Enterokinase reaction buffer. Activation of the pro-KDP1 protein is carried out by treating it with Enterokinase. Enterokinase is removed by appropriate biochemical means after the activation step, and the sample is concentrated, lyophilized and kept at 4° C. until usage.

EXAMPLE 6

This example shows a simple topical skin care composition. The following components are combined utilizing conventional mixing techniques.

| Component | % by Weight of Composition |
|---|---|
| KDP polypeptide | 5 |
| Ethanol | balance to 100 |

This composition is applied twice daily in an amount sufficient to deposit about 0.5 μg/cm² skin for six months, to provide skin conditioning benefits.

EXAMPLE 7

This example shows a simple topical skin care composition. The following components are combined utilizing conventional mixing techniques.

| Component | % by Weight of Composition |
|---|---|
| KDP polypeptide | 0.05 |
| Deionized Water | balance to 100 |

This composition is applied once every three days for three months. Use of an amount sufficient to deposit 120 μg of the active per cm² skin is appropriate to provide skin conditioning benefits.

EXAMPLE 8

This example shows a cream composition prepared by combining the following components utilizing conventional mixing techniques.

| Component | % by Weight of Composition |
|---|---|
| water phase | |
| U.S. Pharmacopia grade H₂O | 63.03 |
| disodium EDTA | 0.13 |
| glycerin | 3 |
| methyl paraben | 0.25 |
| oil phase | |
| propylene glycol dicaprylate/dicaprate | 3 |
| glyceryl stearate | 4 |
| cetyl alcohol | 1 |
| stearyl alcohol | 1 |
| ethoxylated cetyl stearyl alcohol | 1.5 |
| propyl paraben | 0.1 |
| preservative phase | |
| U.S. Pharmacopia grade H₂O | 1.49 |
| butylene glycol | 1.5 |
| benzyl alcohol | 0.5 |
| active solution | |
| KOP polypeptide | 0.03 |
| water | balance to 100 |

The first three phases are mixed with the active solution. The composition is applied once every other day for two months. Use of an amount to deposit 40 μg of the active per cm² skin is appropriate, to provide skin conditioning benefits.

EXAMPLE 9

This example shows a shampoo composition for treating or preventing skin flaking of the scalp. The following components are combined utilizing conventional mixing techniques.

| Component | % by Weight of Composition |
|---|---|
| Sodium lauryl ether sulphate (2EO): 21% AD | 41.4% |
| Lauryl dimethylamino acetic acid betaine: 30% AD | 4 |
| Coconut fatty acid deithanolamine | 1.5 |
| Oleth-3-phosphate (CRODAFOS N 3 Acid ®; Croda) | 1 |
| PEG-15 tallow polyamine (POLYQUART H ®; Henkel): 50% active | 1.5 |
| Preservative, coloring matter, salt | 0.58 |
| Perfume | qs |
| KDP polypeptide | 11 |
| Water | balance to 100 |

EXAMPLE 10

This example shows a hair conditioning composition for treating or preventing skin flaking of the scalp. The following components are combined utilizing conventional mixing techniques.

| Component | % by Weight of Composition |
|---|---|
| Dimethicone/Cyclomethicone | 4.2 |
| Stearamidopropyl dimethylamine | 1 |
| Cetyl alcohol | 0.9 |
| Ditallow dimethyl ammonium | 0.75 |
| Stearyl alcohol | 0.6 |
| Hydroxyethyl cellulose | 0.5 |
| Glyceryl monostearate | 0.25 |
| Citric acid anhydrous | 0.22 |

-continued

| Component | % by Weight of Composition |
|---|---|
| Preservative | 0.0005 |
| Perfume | 0.26 |
| KDP polypeptide | 8 |
| Water | balance to 100 |

EXAMPLE 11

The following granular laundry detergent compositions A to D were prepared in accord with the invention:

| Component | % by Weight of Composition | | | |
|---|---|---|---|---|
| | A | B | C | D |
| base granule | | | | |
| Zeolite A | 30 | 22 | 24 | 10 |
| Sulfate | 10 | 5 | 10 | 7 |
| MA/AA | 3 | — | — | — |
| AA | — | 1.6 | 2 | — |
| MA/AA (1) | — | 12 | — | 6 |
| LAS | 14 | 10 | 9 | 20 |
| C45AS | 8 | 7 | 9 | 7 |
| C45AES | — | 1 | 1 | — |
| Silicate | — | 1 | 0.5 | 10 |
| Soap | — | 2 | — | — |
| Brightener 1 | 0.2 | 0.2 | 0.2 | 0.2 |
| Carbonate | 6 | 9 | 10 | 10 |
| PEG 4000 | — | 1 | 1.5 | — |
| DTPA | — | 0.4 | — | — |
| spray on | | | | |
| C25E9 | — | — | — | 5 |
| C45E7 | 1 | 1 | — | — |
| C23E9 | — | 1 | 2.5 | — |
| Perfume | 0.2 | 0.3 | 0.3 | — |
| dry additives | | | | |
| Carbonate | 5 | 10 | 18 | 8 |
| PVPVI/PVNO | 5 | 10 | 18 | 8 |
| KDP polypeptide | 1 | 1 | 1 | 0.5 |
| Lipase | 0.4 | — | — | 0.4 |
| Amylase | 0.1 | — | — | 0.1 |
| Cellulase | 0.1 | 0.2 | 0.2 | 0.1 |
| NOBS | — | 4 | — | 4.5 |
| PB1 | 1 | 5 | 1.5 | 6 |
| Sulfate | 4 | 5 | — | 5 |
| SRP1 | — | 0.4 | — | — |
| Suds suppressor | — | 0.5 | 0.5 | — |
| Misc./minor to 100% | | | | |

AA: Sodium polyacrylate polymer of average molecular weight 4,500.
Amylase: Amylolytic enzyme, having 1.6% by weight of active enzyme, sold by NOVO Industries A/S under the tradename Termamyl 120T.
Brightener 1: Disodium 4,4'-bis(2-sulphostyryl)biphenyl.
Carbonate: Anydrous sodium carbonate with a particle size between 200 $\mu$m and 900 $\mu$m.
Cellulase: Cellulytic enzyme, having 0.23% by weight of active enzyme, sold by NOVO Industries A/S under the tradename Carezyme.
CxyAS: Sodium $C_{1x}$–$C_{1y}$ alkyl sulfate.
CxyEz: $C_{1x}$–$C_{1y}$ predominantly linear primary alcohol condensed with an average of z moles of ethylene oxide.
CxyEzS: Sodium $C_{1x}$–$C_{1y}$ alkyl sulfate condensed with z moles of ethylene oxide.
DTPA: Diethylene triamine pentaacetic acid.
LAS: Sodium linear $C_{11-13}$ alkyl benzene sulfonate.
Lipase: Lipolytic enzyme, having 2.0% by weight of active enzyme, sold by NOVO Industries A/S under the tradename Lipolase.
MA/AA: Copolymer of 1:4 maleic/acrylic acid, average molecular weight about 70,000.
MA/AA (1): Copolymer of 4:6 maleic/acrylic acid, average molecular weight about 10,000.
NOBS: Nonanoyloxybenzene sulfonate in the form of the sodium salt.
PB1: Anhydrous sodium perborate bleach of nominal formula $NaBO_2 \cdot H_2O_2$.
$PEG_x$: Polyethylene glycol, with a molecular weight of x (typically 4,000).
PVNO: Polyvinylpyridine N-oxide polymer, with an average molecular weight of 50,000.
PVPVI: Copolymer of polyvinylpyrolidone and vinylimidazole, with an average molecular weight of 20,000.
Silicate: Amorphous sodium silicate ($SiO_2:Na_2O=2.0:1$).
Soap: Sodium linear alkyl carboxylate derived from an 80/20 mixture of tallow and coconut fatty acids.
SRP 1: Anionically end capped poly esters.
Sulfate: Anhydrous sodium sulfate.
Zeolite A: Hydrated sodium aluminosilicate of formula $Na_{12}(AlO_2SiO_2)_{12} \cdot 27H_2O$ having a primary particle size in the range from 0.1 to 10 micrometers (weight expressed on an anhydrous basis).

It is understood that the examples and embodiments described herein are for illustrative purposes only and that various modifications or changes in light thereof will be suggested to one skilled in the art without departing from the scope of the present invention.

What is claimed is:

1. An isolated polypeptide comprising an amino acid sequence as shown in:
   a) SEQ ID NO; 2,
   b) positions 1–227 of SEQ ID NO: 2, or
   c) positions 39–185 of SEQ ID NO: 2.

2. An isolated polynucleotide comprising a nucleotide sequence as shown in:
   a) SEQ ID NO: 1,
   b) positions 291–1172 of SEQ ID NO: 1,
   c) positions 1–1172 of SEQ ID NO: 1, or
   d) positions 291–1499 of SEQ ID NO: 1.

3. An isolated polynucleotide encoding the polypeptide of claim 1.

4. An expression system comprising the polynucleotide of claim 3.

5. A composition comprising the polypeptide of claim 1.

6. The composition of claim 5, wherein the composition is a skin care composition.

7. A method of treating or preventing skin flaking comprising topical application of a composition comprising the polypeptide of claim 1.

* * * * *